United States Patent
Lonn et al.

(10) Patent No.: US 6,856,666 B2
(45) Date of Patent: Feb. 15, 2005

(54) MULTI MODALITY IMAGING METHODS AND APPARATUS

(75) Inventors: Albert Henry Roger Lonn, Beaconsfield (GB); Jiang Hsieh, Brookfield, WI (US); Charles William Stearns, New Berlin, WI (US); Edward Henry Chao, Oconomowoc, WI (US); Brian Grekowicz, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 61 days.

(21) Appl. No.: 10/428,906

(22) Filed: May 2, 2003

(65) Prior Publication Data

US 2004/0066909 A1 Apr. 8, 2004

Related U.S. Application Data

(60) Provisional application No. 60/416,072, filed on Oct. 4, 2002.

(51) Int. Cl.$^7$ .................................................. A61B 6/03
(52) U.S. Cl. ................................ 378/8; 378/4; 378/19; 378/901
(58) Field of Search ............................ 378/4, 8, 15, 19, 378/901

(56) References Cited

U.S. PATENT DOCUMENTS

| | | | |
|---|---|---|---|
| 4,136,388 A | 1/1979 | Lindquist | |
| 4,189,775 A | 2/1980 | Inouye et al. | |
| 4,305,127 A | 12/1981 | Heuscher | |
| 4,446,521 A | 5/1984 | Inouye | |
| 4,550,371 A | 10/1985 | Glover et al. | |
| 4,878,169 A | 10/1989 | Toner et al. | |
| 5,043,890 A | 8/1991 | King | |
| 5,276,614 A | 1/1994 | Heuscher | |
| 5,640,436 A | 6/1997 | Kawai et al. | |
| 5,953,388 A | 9/1999 | Walnut et al. | |
| 6,307,909 B1 | 10/2001 | Flohr et al. | |
| 2003/0212320 A1 * | 11/2003 | Wilk et al. | 600/407 |

* cited by examiner

*Primary Examiner*—David V Bruce
(74) *Attorney, Agent, or Firm*—Carl B. Horton, Esq.; Armstrong Teasdale LLP

(57) ABSTRACT

A method includes scanning an object in a first modality having a first field of view to obtain first modality data including fully sampled field of view data and partially sampled field of view data. The method also includes scanning the object in a second modality having a second field of view larger than the first field of view of obtain second modality data, and reconstructing an image of the object using the second modality data and the first modality partially sampled field of view data.

40 Claims, 11 Drawing Sheets

A          B

C          D

MULTI MODALITY IMAGING METHODS AND APPARATUS

CROSS REFERENCE TO RELATED APPLICATIONS

This application claims the benefit of U.S. provisional application No. 60/416,072 filed Oct. 4, 2002.

BACKGROUND OF THE INVENTION

This invention relates generally to imaging systems capable of scanning objects in multi modalities and more particularly to multi-modality systems wherein the modalities have different fields of views.

The present invention is directed toward multi-modal imaging systems capable of scanning using different modalities, such as, for example, but not limited to, Positron Emission Tomography (PET) and Computed Tomography (CT). The difference between multi-mode and multi-modality is that multi-mode systems are utilized to perform scans in different modes (e.g., a fluoro mode and a tomosynthesis mode), while a multi-modal system (multi-modality system) is utilized to perform scans in different modalities (e.g., CT and PET). It is contemplated that the benefits of the invention accrue to all multi-modality imaging systems, such as, for example, but not limited to, a CT/PET imaging system.

At least some multi-modality systems have different fields of views (FOVs) for the different modalities. For example, a CT/PET system may have a CT FOV which is smaller than a PET FOV, and under some scanning conditions, portions of a patient may extend beyond the region measured by a CT detector, which may lead to image artifacts and an incomplete representation of the imaged object. Some known methods have been published that address the artifact reduction but not the imaging of the portion of the patient that is outside the CT FOV.

In such multi-modality systems, such as, for example, an integrated PET-CT system there is an inherent registration of the PET and CT images the system acquires. Since the patient lies still on the same table during the PET and CT portions of the acquisition, the patient will be in a consistent position and orientation during the two acquisitions, greatly simplifying the process of correlating and fusing the CT and PET images. This allows the CT image to be used to provide attenuation correction information for the reconstruction of the PET image, and allows an image reader to easily correlate the anatomic information presented in the CT image and the functional information presented in the PET image. However, it is desirable to provide attenuation information for the reconstruction of the PET image of the portion of the patient that extends beyond the CT FOV. It is also desirable to provide accurate attenuation information for the PET image inside the FOV (Note that artifacts caused by truncation produce biased attenuation information).

BRIEF DESCRIPTION OF THE INVENTION

In one aspect, a method includes scanning an object in a first modality having a first field of view to obtain first modality data including fully sampled field of view data and partially sampled field of view data. The method also includes scanning the object in a second modality having a second field of view larger than the first field of view to obtain second modality data, and reconstructing an image of the object using the second modality data and the first modality partially sampled field of view data.

In another aspect, an imaging apparatus is provided. The apparatus includes a Computed Tomography (CT) system including an x-ray source and a detector responsive to x-rays positioned to receive x-rays emitted from the source, a Positron Emission Tomography (PET) system including a detector responsive to a gamma ray, and a computer operationally coupled to the CT system and the PET system. The computer is configured to receive data from a CT scan of an object, the data including fully sampled field of view data and partially sampled field of view data, augment the received partially sampled field of view data using the fully sampled field of view data, receive data from a PET scan of the object, and reconstruct an image of the object using the received PET data and the augmented partially sampled field of view data.

In another aspect, a computer readable medium encoded with a program is provided. The program is configured to instruct a computer to augment partially sampled field of view data from a first modality using fully sampled field of view data from the first modality, and reconstruct an image in a second modality using the augmented first modality data.

The invention also includes a method for use with first and second image data sets corresponding to first and second fields of view (FOV), respectively, the first data set including a plurality of projection views that each include first through last attenuation measurements corresponding to first through last parallel trajectories through the first FOV, respectively, the first FOV smaller than and included within the second FOV such that only area common to the first and second FOVs is traversed by each of the projection views and area within the second FOV and outside the first FOV is traversed by only a sub-set of the projection views, the method comprising the steps of using the attenuation measurements from at least one projection view to augment the attenuation measurements from at least one other projection view to add attenuation measurements to the at least one other projection view corresponding to trajectories that traverse at least a portion of the second FOV, using the augmented projection views to compensate the second data set for attenuation and combining the compensated second data set to construct an image.

The invention further includes a method for use with a structural data set and a functional data set indicating structural and functional characteristics of an imaged object, the structural and functional sets corresponding to first and second fields of view (FOV), respectively, the structural data set including a plurality of projection views that each include first through last attenuation measurements corresponding to first through last parallel trajectories through the first FOV, respectively, the first FOV smaller than and included within the second FOV such that only area common to the first and second FOVs is traversed by each of the projection views and area within the second FOV and outside the first FOV is traversed by only a sub-set of the projection views, the method comprising the steps of, for each projection view, summing up all of the attenuation measurements to generate a view attenuation measurement, identifying the maximum view attenuation measurement and for each of at least a sub-set of the view attenuation measurements that is less than the maximum attenuation measurement, augmenting the associated projection view to generate an augmented attenuation view such that the sum of all of the attenuation measurements of the augmented view is substantially similar to the maximum attenuation measurement using the augmented projection views and the un-augmented projection views to compensate the second data set for attenuation and combining the compensated second data set to construct an image.

In addition, the invention includes a method for use with first and second detectors arranged to collect first and second data sets from a plurality of projection angles about first and second fields of view (FOVs), respectively, the data at each projection angle including a projection view, the second FOV larger than and including the first FOV such that each first set projection view only traverses a portion of the second FOV, the method for generating an image of an object that resides within the second FOV and comprising the steps of, collecting the first and second data sets, identifying at least one first set projection view that likely encompasses the entire object as a complete projection view, where the object extends outside the first FOV: identifying first set projection views that the object extends out of as truncated projection views, using the complete projection view data to augment the data of each truncated projection view thereby generating an augmented first set, combining the augmented first set and the second set to generate a compensated second set and combining the compensated second set to generate an image.

Moreover, the invention includes an imaging apparatus for use with a structural data set and a functional data set indicating structural and functional characteristics of an imaged object, the structural and functional sets corresponding to first and second fields of view (FOV), respectively, the structural data set including a plurality of projection views that each include first through last attenuation measurements corresponding to first through last parallel trajectories through the first FOV, respectively, the first FOV smaller than and included within the second FOV such that only area common to the first and second FOVs is traversed by each of the projection views and area within the second FOV and outside the first FOV is traversed by only a sub-set of the projection views, the apparatus comprising a computer configured to, for each projection view, sum up all of the attenuation measurements to generate a view attenuation measurement, identify the maximum view attenuation measurement and for each of at least a sub-set of the view attenuation measurements that is less than the maximum attenuation measurement, augment the associated projection view to generate an augmented attenuation view such that the sum of all of the attenuation measurements of the augmented view is substantially similar to the maximum attenuation measurement, use the augmented projection views and the un-augmented projection views to compensate the second data set for attenuation and combine the compensated second data set to construct an image.

DETAILED DESCRIPTION OF THE INVENTION

Figure 1:
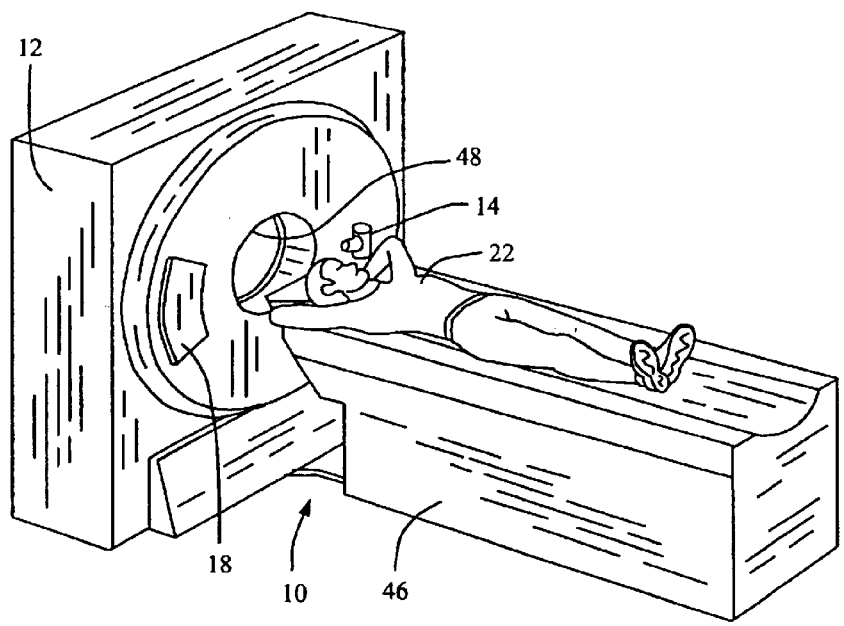
FIG. 1 is a pictorial view of a CT imaging system embodiment.

There is herein provided truncation compensation methods and apparatus for Extended Field-of-View in Rotating Acquisition Systems. As explained in greater detail below, in one aspect, a method is at least partially based on a property that for parallel sampling geometry, the total amount of attenuation integrated over all channels for a parallel sampling geometry is independent of the projection angle. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two dimensional slice taken through the object.

To further improve the performance of the CT system, multi-slice CT systems are built. In such systems, multiple projections are acquired simultaneously with multiple detector rows. Similar to the case of helical scan, weighting functions are applied to the projection data prior to the filtered backprojection process.

At least some CT systems are configured to also perform Positron Emission Tomography (PET) and are referred to as CT/PET systems (and PET/CT systems). Positrons are positively charged electrons (anti-electrons) which are emitted by radio nuclides that have been prepared using a cyclotron or other device. The radio nuclides most often employed in diagnostic imaging are fluorine-18 (18F), carbon-11 (11C), nitrogen-13 (13N), and oxygen-15 (15O). Radio nuclides are employed as radioactive tracers called "radiopharmaceuticals" by incorporating them into substances such as glucose or carbon dioxide. One common use for radiopharmaceuticals is in the medical imaging field.

To use a radiopharmaceutical in imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism, fatty acid metabolism and protein synthesis. Hereinafter, in the interest of simplifying this explanation, an organ to be imaged including a vessel will be referred to generally as an "organ of interest" and the invention will be described with respect to a hypothetical organ of interest.

After the radiopharmaceutical becomes concentrated within an organ of interest and while the radio nuclides decay, the radio nuclides emit positrons. The positrons travel a very short distance before they encounter an electron and, when the positron encounters an electron, the positron is annihilated and converted into two photons, or gamma rays. This annihilation event is characterized by two features which are pertinent to medical imaging and particularly to medical imaging using photon emission tomography (PET). First, each gamma ray has an energy of approximately 511 keV upon annihilation. Second, the two gamma rays are directed in substantially opposite directions.

In PET imaging, if the general locations of annihilations can be identified in three dimensions, a three dimensional image of an organ of interest can be reconstructed for observation. To detect annihilation locations, a PET camera is employed. An exemplary PET camera includes a plurality of detectors and a processor which, among other things, includes coincidence detection circuitry.

The coincidence circuitry identifies essentially simultaneous pulse pairs which correspond to detectors which are essentially on opposite sides of the imaging area. Thus, a simultaneous pulse pair indicates that an annihilation has occurred on a straight line between an associated pair of detectors. Over an acquisition period of a few minutes millions of annihilations are recorded, each annihilation associated with a unique detector pair. After an acquisition period, recorded annihilation data can be used via any of several different well known back projection procedures to construct the three dimensional image of the organ of interest.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
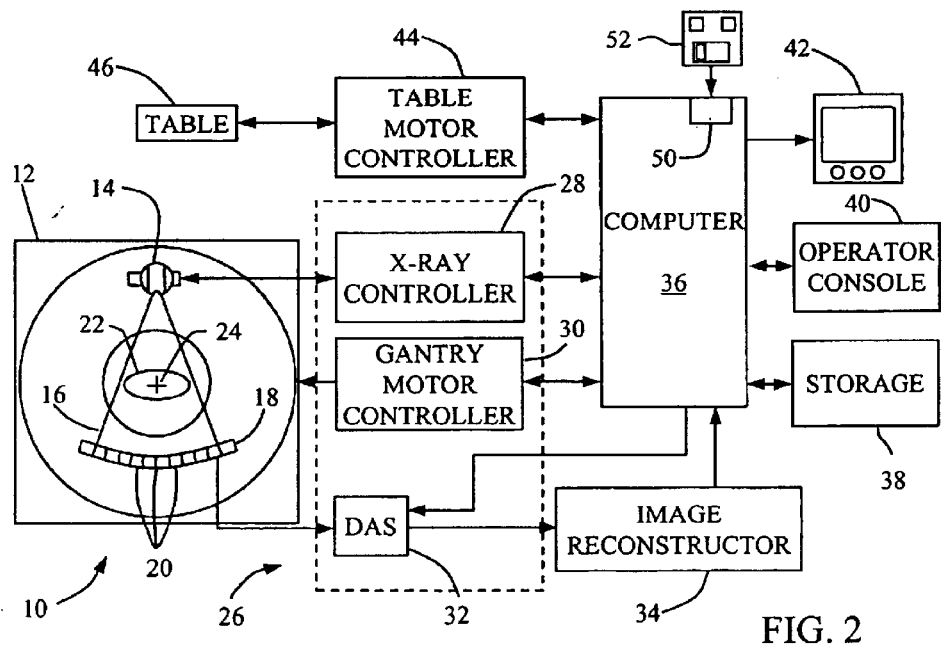
FIG. 2 is a block schematic diagram of the system illustrated in FIG. 1.

Referring to FIGS. 1 and 2, a multi-modal imaging system 10 is illustrated, and includes a first modality unit and a second modality unit (not shown in FIGS. 1 and 2). The two modality units enable system 10 to scan an object in a first modality using the first modality unit and to scan the object in a second modality using the second modality unit. System 10 allows for multiple scans in different modalities to facilitate an increased diagnostic capability over single modality systems. In one embodiment, multi-modal imaging system 10 is a Computed Tomography/Positron Emission Tomography (CT/PET) imaging system 10, and CT/PET system 10 is shown as including a gantry 12 representative of a "third generation" CT imaging system in combination with PET circuitry. In alternative embodiments, modalities other than CT and PET are employed with system 10. Gantry 12 includes the first modality unit which has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence allows estimation of the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, a multislice detector array 18 includes a plurality of parallel detector rows of detector elements 20 such that projection data corresponding to a plurality of slices can be acquired simultaneously during a scan.

Rotation of gantry 12 and the operation of x-ray source 14 are governed by a control mechanism 26 of CT/PET system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. CT/PET system 10 also includes a plurality of PET detectors (not shown) including a plurality of detectors. The PET detectors and detector array 18 both detect radiation and are both referred to herein as radiation detectors. In one embodiment, CT/PET system 10 is a Discovery LS CT/PET system commercially available from General Electric Medical Systems, Waukesha Wis., and configured as herein described. In another embodiment, CT/PET system 10 is a Hawkeye CT/PET system also commercially available from General Electric Medical Systems, Waukesha Wis., and configured as herein described.

Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station.

Figure 3:
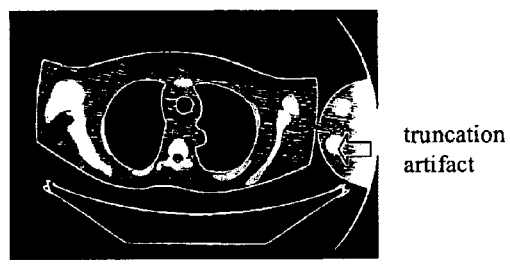
FIG. 3 illustrates truncated artifacts.

Under some scanning conditions, portions of patient 22 extend beyond the region measured by detector 18, which may lead to image artifacts and an incomplete representation of the imaged object. Some known methods have been published that address the artifact reduction but not the imaging of the portion of the patient that is outside the field of view (FOV). However, it is desirable to image the portion of the patient that extends beyond the FOV. This is useful in many fields including Oncology, Spin Angiography, Fused imaging systems, and In Economy CT Scanners. The current hardware of known multi-slice CT scanner limits the reconstruction field of view (FOV) to about 50 centimeters (cm.). Although this is sufficient for most clinical applications, it is desirable to expand the FOV to image objects outside this FOV. This may have particular advantages for applications such as oncology or CT/PET. For oncology applications, a larger FOV is desired. This is mainly due to the fact that for radiation treatment planning, the limbs of the patient are often positioned outside the scan FOV for better tumor positioning. The known CT reconstruction algorithms ignore the truncated projections and produce images with severe artifacts. These artifacts may affect an accurate estimation of the attenuation path for treatment planning. One phantom example is shown in FIG. 3 which illustrates a truncation artifact. For Fused Imaging systems such as CT/PET (Computed Tomography/Positron Emission Tomography) the FOV of the PET system may not match the existing CT design. It is desirable to have a consistent FOV between the CT and the other imaging system, CT/PET, CT/NUC (CT/Nuclear), or CT/MR (CT/Magnetic Resonance). This correction can be used to adjust the FOV to match. For PET this enables better attenuation correction. Herein described is an algorithmic approach to increase the reconstruction FOV beyond the FOV limited by the detector hardware. This correction algorithm can be applied to various reconstruction algorithms including, but not limited to, Full scan, Halfscan/segment and the cardiac sector based algorithms. Additionally, system 10 is configured to employ the herein described algorithms.

Figure 4:
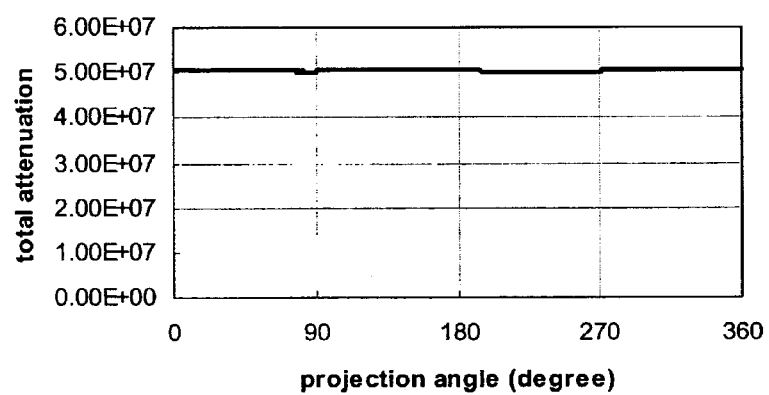
FIG. 4 is a graph showing a total attenuation integrated over all channels as a function of projection angle for a chest phantom.
Figure 5:
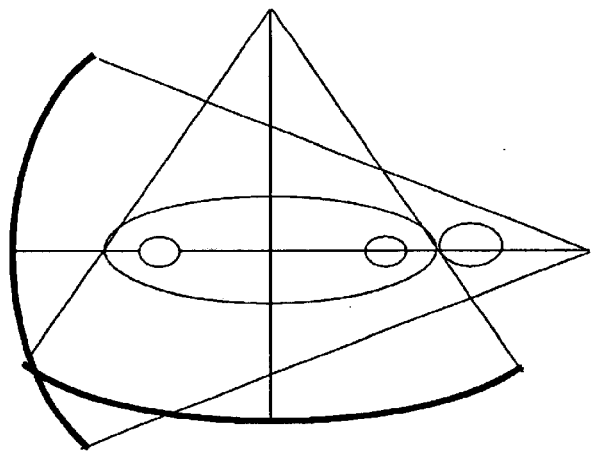
FIG. 5 is an illustration of truncation in a clinical setting.
Figure 6:
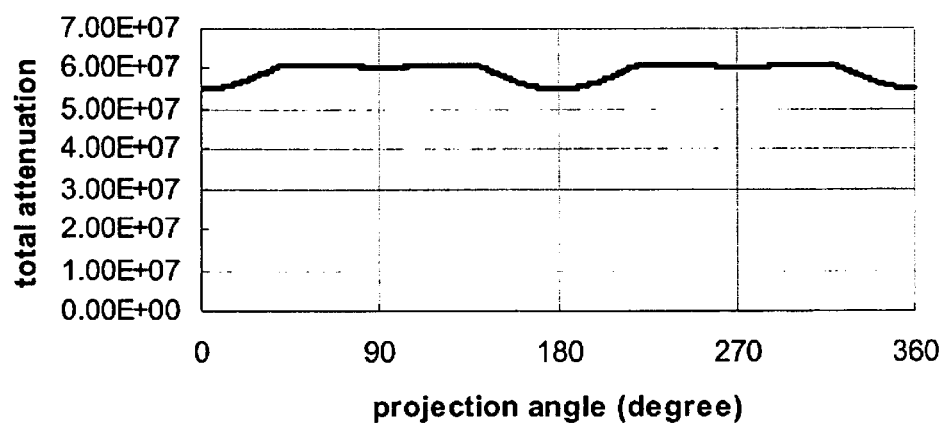
FIG. 6 is a graph illustrating the impact of truncation projection on a total attenuation.
Figure 7:
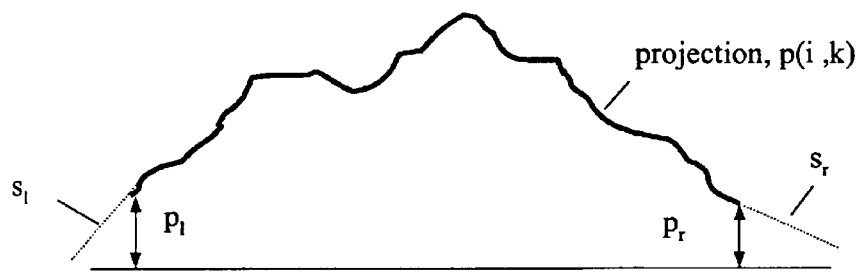
FIG. 7 is an illustration of slopes and boundaries estimation.

FIG. 4 shows the total amount of attenuation (integrated over all channels) of a parallel sampling geometry plotted as a function of projection angle for a chest phantom scan. The parallel sampling is obtained by rebinning the original fan beam data with techniques known in the art. Note that the curve is nearly a horizontal line. This property does not exist, however, for the fan beam sampling geometry. When the scanned object is outside the scan field-of-view (FOV), this property is no longer valid. The amount of deficit is equal to the portion of the object that is outside the projection FOV. In nearly all clinical cases, the projection truncation occurs only in a portion of the projection angles, as illustrated in FIG. 5. In this example, the projection taken at a 3 o'clock position is free of truncation and the projection taken at a 12 o'clock is severely truncated. Therefore, one can rely on the un-truncated projections (i.e., positions around 3 o'clock in FIG. 5, for example) to estimate the amount of truncation for the truncated views (e.g., positions around 12 o'clock for the example in FIG. 5). One early step in the correction process is to perform software fan-beam to parallel-beam rebinning on the pre-processed projections. In one embodiment, that early step is the first step. This process is well known in the art and does not require special data collection. Once the rebinning is completed, the projections are integrated over all detector channels to obtain the total attenuation curve, as shown in FIG. 6. Note, the dips in the total attenuation curve correspond to views with truncation. The flat portion of the curve corresponds to the views in which no object truncation occurs. Once the total amount of the object outside the FOV is estimated, the next step is to estimate the distribution of the missing projection. To achieve this objective, in one embodiment, one first calculates the boundary reading, $p_l$ and $P_r$ as shown below in equation 1, in the truncated projection, as shown in FIG. 7 which illustrates a slope and boundary estimation. To reduce noise, in one embodiment, the average of m number of samples is used. M=3 has empirically been shown to be useful in reducing noise. In other embodiments, m is greater than 1 and less than 5.

Equation 1:

$$p_l = \frac{1}{m}\sum_{i=1}^{m} p(i, k) \text{ and } p_r = \frac{1}{m}\sum_{i=1}^{m} p(N - i, k)$$

where N is the number of detector channels, and k is the projection view index. In addition, in one embodiment, the slopes, $s_l$ and $S_r$ near both ends are also estimated. The slope estimation is performed by fitting n samples near the ends with a first order polynomial. N=5 has empirically shown to be useful. In one embodiment, n is greater than 2 and less than 8. In another embodiment, n is greater than 3 and less than 7.

To further improve the reliability of the estimation, projections are used which are acquired from neighboring detector rows. Since human anatomy typically does not change quickly over a small distance (a few millimeters), the boundary samples and the slopes estimated from the neighboring rows do not typically vary significantly. Therefore, the estimated parameters ($p_l$, $p_r$, $s_l$, and $s_r$) can be the weighted average of the values calculated from several detector rows. Based on the boundary and slope information, one estimates a location and the size of a cylindrical water object that can be best fitted to the truncated projection. If we denote the attenuation coefficient of water $\mu_w$, the radius of the cylinder R, and the distance from the cylinder center X, the projection value, p(x), and slope, p'(x), can be described by the following equation.

Equation 2:

$$p(x) = 2\mu_w\sqrt{R^2 - x^2} \text{ and } p'(x) = \frac{-2\mu_w x}{\sqrt{R^2 - x^2}}$$

Since both p(x) and p'(x) are calculated at the truncated projection boundaries, the goal is to estimate R and x so that one obtains the size and location of the cylinder that is to be appended to the missing projection. The formula to estimate these parameters can be described by the following equations:

$$x_l = \frac{-(s_l)(p_l)}{4\mu_w^2} \text{ and } R_l = \sqrt{\frac{p_l^2}{4\mu_w^2} + x_l^2} \quad \text{Eq. 3}$$

$$x_r = \frac{-(s_r)(p_r)}{4\mu_w^2} \text{ and } R_r = \sqrt{\frac{p_r^2}{4\mu_w^2} + x_r^2} \quad \text{Eq. 4}$$

Figure 8:
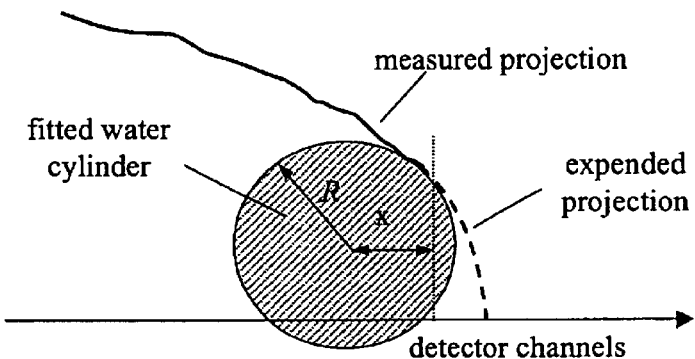
FIG. 8 is an illustration of fitted water cylinder for truncated projection.

The variables represent the estimated location and the size of the cylindrical objects that need to be extended from the truncated object. Once these parameters are determined, the expended projections can be calculated using equation (2). The process is illustrated in FIG. 8 of a water filled cylinder for truncated projection.

In this example, a cylindrical water phantom was used for simplicity. In reality, other object shapes, such as an elliptical cylinder, can also be used to increase the flexibility. If a priori information is available on the characteristics of the scanned object, the information can of course be used in the shape selection of the appending object. Iterative methods can be used to estimate the missing projection data.

Figure 9:
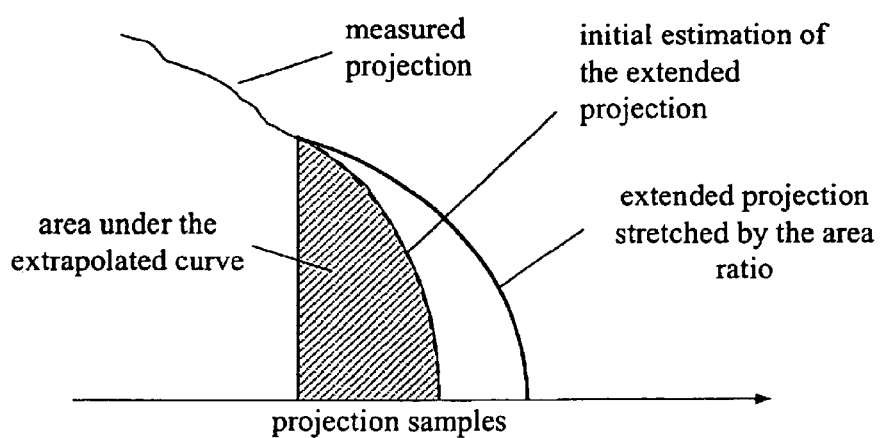
FIG. 9 is an illustration of a projection extension scaled by the expected total attenuation.

The estimated cylinders on both ends of the projection do not always recover the total amount of attenuation for the entire projection, since these objects are determined solely from the slope and boundary samples. None of the information derived from the total attenuation curve (FIG. 6) is used. To ensure proper compensation for the total attenuation loss, the attenuation distribution of the left side, $T_l$, verses the right side, $T_r$, is determined based on the magnitude of $p_l$ and $p_r$.

$$T_l = \frac{p_l T}{p_l + p_r} \text{ and } T_r = \frac{p_r T}{p_l + p_r} \quad \text{Eq. 5}$$

where T is the total amount of loss in attenuation determined from FIG. 6. Additionally, if the amount of attenuation under the extended curve is insufficient to make up for the attenuation loss, the estimated projection is stretched to fulfill the attenuation deficits, as illustrated in FIG. 9 wherein the projection extension is scaled by the expected total attenuation. In one embodiment, the calculation process is as follows. One first calculates the ratio of the expected total attenuation (shown in Eq. (5)) over the area under the extended projection curve (shown by the shaded region in FIG. 9). If the ratio is larger than unity, the x-axis is scaled by the ratio so that the initial estimated projection (shown by the dotted line in FIG. 9) is further expanded (shown by the solid thick line in FIG. 9). Similarly, if the ratio is significantly smaller than unity, the expanded projection can be compressed in x.

Figure 10:
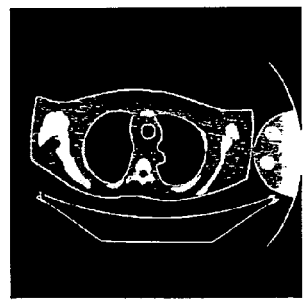
FIG. 10 illustrates a plurality of images.
Figure 10:
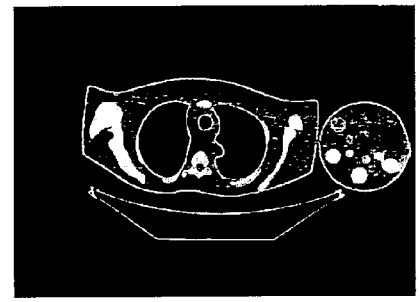
Figure 10:
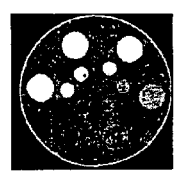
Figure 10:
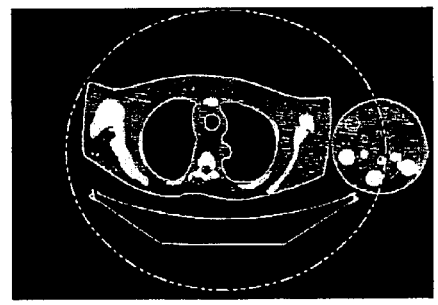

FIG. 10 shows an example of the reconstructed phantom images without and with correction. A shoulder phantom was scanned in an axial scan mode with a 4×1.25 mm detector configuration. A 15 cm plastic phantom was attached to the shoulder phantom in such a way that the edge of the plastic phantom is near the boundary of the 65 cm FOV. The truncated object is nearly completely recovered. Note that FIG. 10(a) was reconstructed with a 50 cm FOV without truncation correction (current product limit) and FIG. 10(b) was reconstructed with 65 cm FOV with the herein described methods and apparatus. For reference, the phantom that is partially truncated is shown in FIG. 10(c).

Although the above described system and methods uses only the conservation of total attenuation, the magnitude, and the slope of the boundary samples to estimate the missing projection distribution, additional information can also be used for the estimation. For example, one could use the Helgason-Ludwig Condition (HL condition) for tomography to further refine the above technique. Additionally, different thresholds can be placed to ensure that the algorithm functions properly under erroneous measurement conditions. For example, one could set the upper and lower limits on the stretch ratio described in FIG. 9 to prevent the condition of increased error due to unreliable measurement. In addition, the slope calculation of $s_l$ and $s_r$ can be set such that it falls within a reasonable range. If the characteristic of the material of the scanned object is known to be significantly different from water, one can also use the attenuation coefficients of the known material (instead of water) to perform size and location calculations shown in Eqs. (3) and (4). Additionally, information obtained from other modality can be used to further refine the estimation of the missing object. For example, reconstructed PET images (without attenuation correction) could help to estimate the object boundary if some level of radioactive uptake is present. This information can be fed to the CT image reconstruction to further refine the truncation correction.

Because the interpolated data does not have the same image quality as data within the fully sampled FOV it may be useful to tag the image where the FOV becomes extrapolated. FIG. 10(d) illustrates the boundary is tagged by a dotted line. This could also be done with a color code or shift in the CT Number. Because the tag may impact the ability to view the image data an easy way is provided to turn on and off the tagging. A user of system 10 is allowed to turn on or off the tagging.

Figure 11:
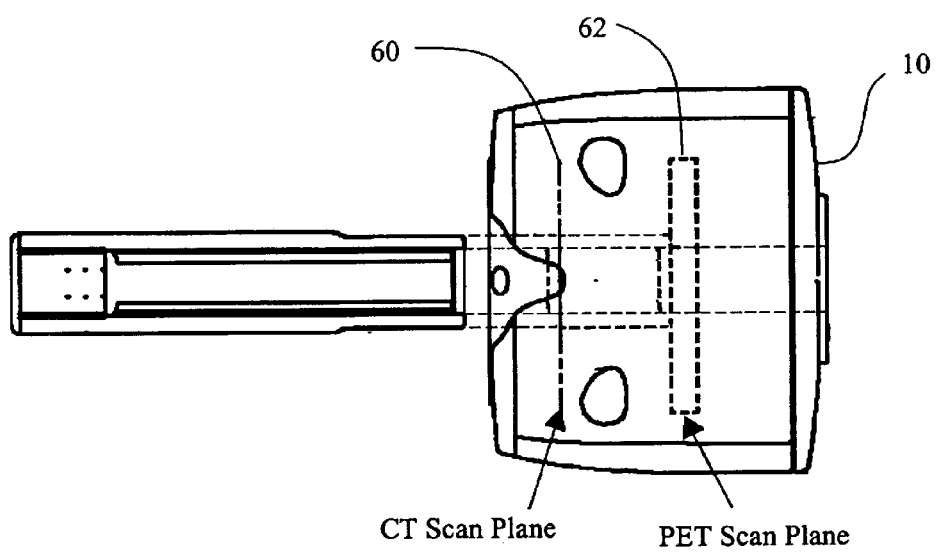
FIG. 11 is a top view of the system shown in FIGS. 1 and 2 and illustrating a first modality scan plane and a second modality scan plane.

FIG. 11 is a top view of system 10 illustrating a first modality scan plane 60 and a second modality scan plane 62. In an exemplary embodiment, the first modality is CT and the second-modality is PET.

Figure 12:
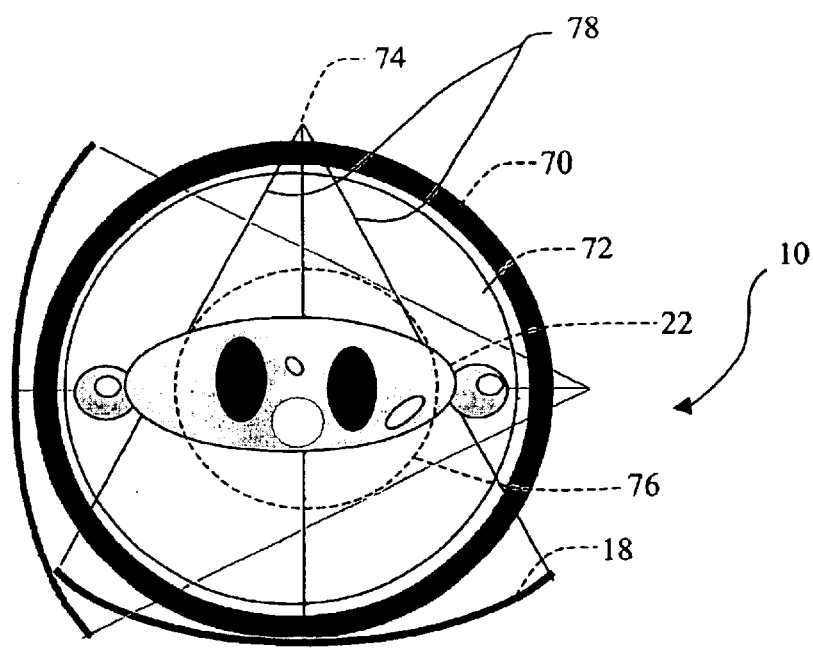
FIG. 12 illustrates transaxial imaging fields of the first and second modalities.

FIG. 12 illustrates transaxial imaging fields of the first and second modalities. The transaxial imaging arrangement illustrates a PET detector 70 arranged around a patient aperture 72 and images photons emanating from patient 22 or other test object positioned within patient aperture 72. Source 14 includes an X ray tube (not shown) with a focal spot 74 positioned at a focus of array of X-ray detectors 18 which measure the transmitted X-ray intensity through patient 22. The X-ray tube and detector 18 are rigidly held together on a frame which rotates around patient aperture 72. During the course of rotation, measurements are continuously made within a "fully sampled field of view" 76. The attenuation of x-rays traversing any areas of object 22 positioned between fully sampled field of view 76 and patient aperture 72 is measured at a limited range of rotation angles, and this region is referred to as the "partially sampled field of view" region. In other words, portions that are within fully sampled field of view 76 are positioned within a fan 78 such that measurements are obtainable at all gantry angles, and the data collected is defined as fully sampled field of view data. Some portions, however, are within fan 78 at some angles but are outside fan 78 at other angles, and the data collected regarding these portions is defined as partially sampled field of view data.

Figure 13:
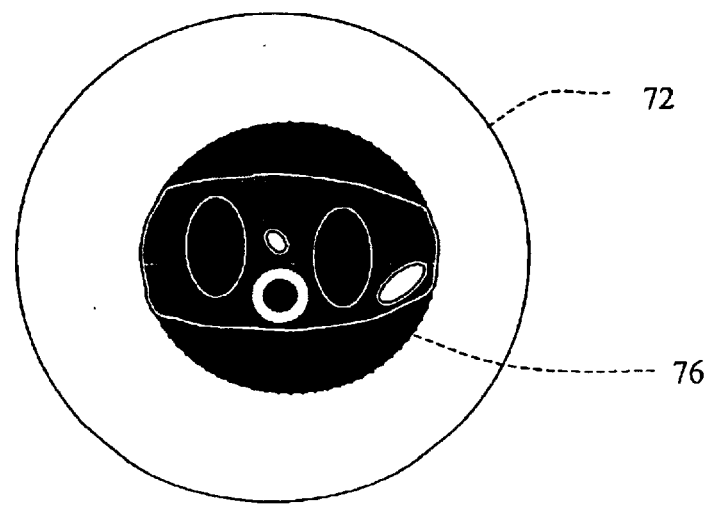
FIG. 13 illustrates a normal reconstructed image of a CT detector that is restricted to fully sampled field of view.

FIG. 13 illustrates a normal reconstructed image of a CT detector that is restricted to fully sample field of view 76, where patient 22 (not shown in FIG. 13) extends outside FOV. Normally the CT reconstruction process only reconstructs fully sampled field of view 76 resulting in an image similar to FIG. 13 where any object or portion of an object which extends into the partially sampled field of view are absent. Another artifact observed with some truncated CT reconstructions is an apparent increase in attenuation at the junction of large amounts of truncated attenuation, as observed in FIG. 16F. When the truncated image is used to measure the patient attenuation, the attenuation is underestimated because of the missing objects and could be overestimated in some lines of response because of the overshoot at the edge of the CT FOV.

Figure 14:
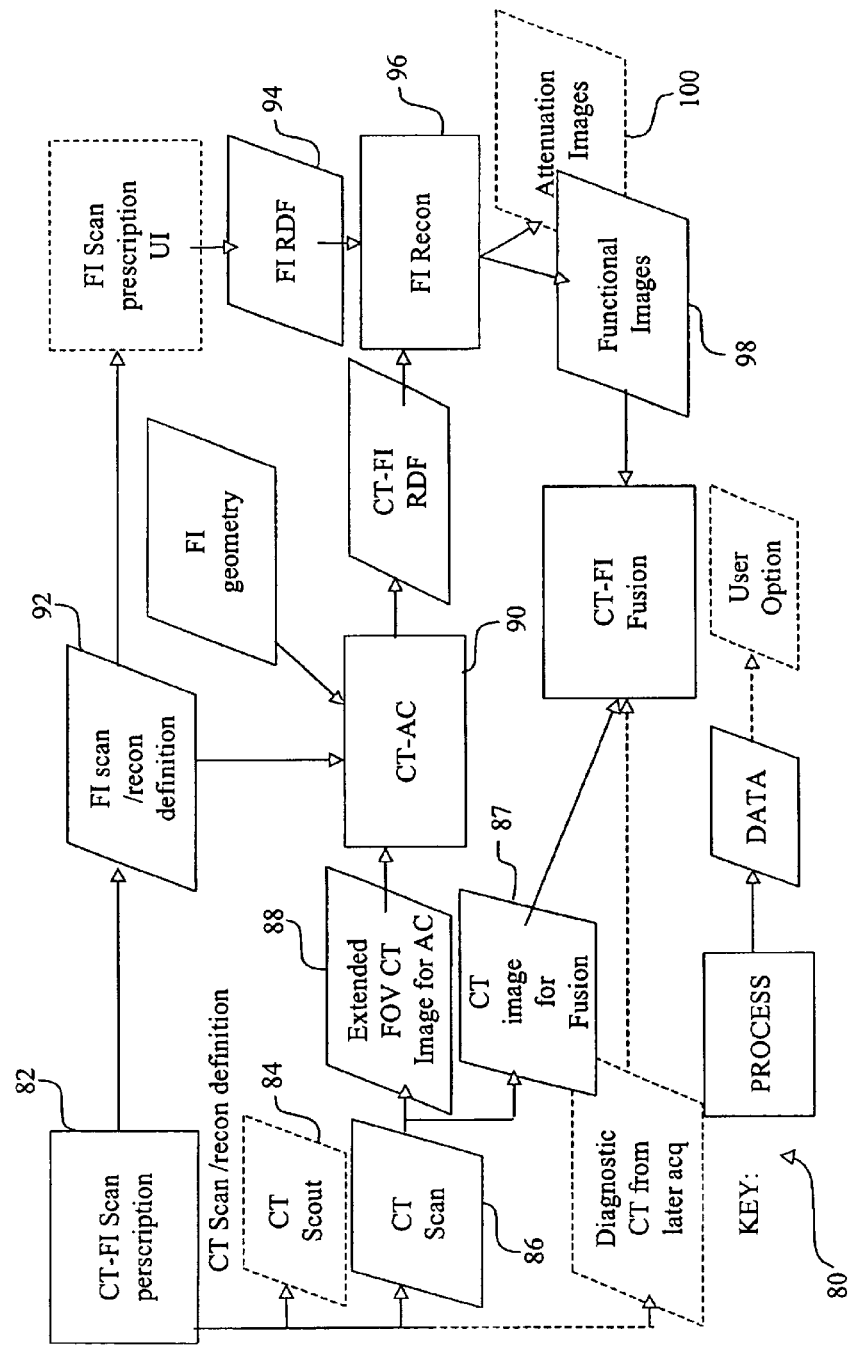
FIG. 14 illustrates a CT-FI (Functional Image) reconstruction flow diagram.

FIG. 14 illustrates a CT-FI (Functional Image) reconstruction flow process 80 which uses extended field of view data from CT to correct attenuation in a PET image, or other functional image such as Single Photon Emission Computed Tomography (SPECT). A CT-FI scan prescription step 82 defines a volume to be scanned and a plurality of reconstruction parameters of a functional image (FI) and a matching CT image for fusion, wherein an optional diagnostic CT is acquired later if desired. After an optional CT Scout 84, a low dose CT scan 86 is performed which is reconstructed twice. Once using the prescribed reconstruction parameters to produce the CT images for fusion 87, and a second time using the above described extended FOV for the CT images for Attenuation Correction 88 (CTAC). A CTAC step 90 converts the CT images into attenuation raw data files, using a FI scan prescription 92 (reconstruction definition) to create a file for each FI slice location and the CT-FI alignment calibration data to align the attenuation measurements to the FI detector readings. An FI acquisition step 94 acquires the emission data in one or more FI FOVs using a Resource Description Framework (RDF) model. An FI reconstruction step 96 uses the CT-FI raw data file to correct the emission data for attenuation and produces a corrected functional image 98, and an optional image 100 showing the attenuation. At a CT-FL Fusion step 102 both the CT and the PET images are received which are inherently aligned and have been panned, zoomed, and filtered as specified in CT-FL scan prescription 82.

CTAC step 90 converts the CT images into attenuation correction files for correction of the emission attenuation. The following describes a method to derive the conversion from CT numbers to attenuation at the required emission energy. The CT image is calibrated in Hounsfield units which represents the attenuation of the X-ray beam with reference to the attenuation of air and water. The CT number of a particular material, CT [material], is computed as follows where $\mu$ represents the linear attenuation coefficient.

$$CT\ [\text{material}] = \frac{1000 * \{\mu[\text{material}] - \mu[\text{water}]\}}{\mu[\text{water}] - \mu[\text{air}]}$$

The CT machine is calibrated at each kV setting to give CT numbers of 0 for water; and −1000 for air. Some materials such as Bone (and to a lesser extent, fat) have a different energy dependence of attenuation, and the CT number of these materials changes with energy. Two different scaling algorithm are used to convert the range of tissue to emission attenuation coefficients.

For CT values less than 0, materials are assumed to have an energy dependence similar to water (e.g., water and tissue) and the attenuation values at the required emission energy keV are obtained as follows:

$$\mu[\text{mat, keV}] - \mu[\text{air, keV}] = \frac{\{\mu[\text{water, keV}] - \mu[\text{air, keV}]\} * \{CTmat + 1000\}}{1000}$$

If the attenuation of air is ignored, this conversion just requires knowledge of the attenuation of water at the emission energy. The effective energy of the scanner is not required, since the scanner is calibrated to give the same soft tissue CT numbers regardless of the scan technique. The emission energy keV, is derived from knowledge of the radioisotope and the type of detection. In the case of PET detectors, the emission energy is 511 keV and in the case of the SPECT detectors, the emission energy is dependent on the isotope and the energy acceptance settings of the detector. Thus PET detectors could use a fixed value for attenuation of water at 511 keV. SPECT detectors could use a table of attenuation values of a range of keV.

For Bone scaling, CT values above 0 are treated as being a mixture of bone and water and the attenuation values are converted from measurements at the X-ray effective energy, $kV_{eff}$, to attenuation values at the required emission energy keV as follows $$\mu[\text{material, keV}] = \mu[\text{water, keV}] +$$
$$\frac{CT[kVp] * \mu[\text{water}, kV_{eff}] * \{\mu[\text{bone, keV}] - \mu[\text{water, keV}]\}}{1000 * \{\mu[\text{bone}, kV_{eff}] - \mu[\text{water}, kV_{eff}]\}}$$

Where CT[kVp] is the CT number of the material measured at the high voltage setting of kVp (kilo-Volt potential). This formula requires values of the attenuation of bone and water at both the effective energy of the CT scanner and at the emission energy. These values can be supplied in the form of tables as follows. A table of attenuation of bone and water at each kVp setting (derived from measurement of effective energy) and a table of attenuation of bone and water for each emission energy (511 eV in the case of PET).

Figure 15:
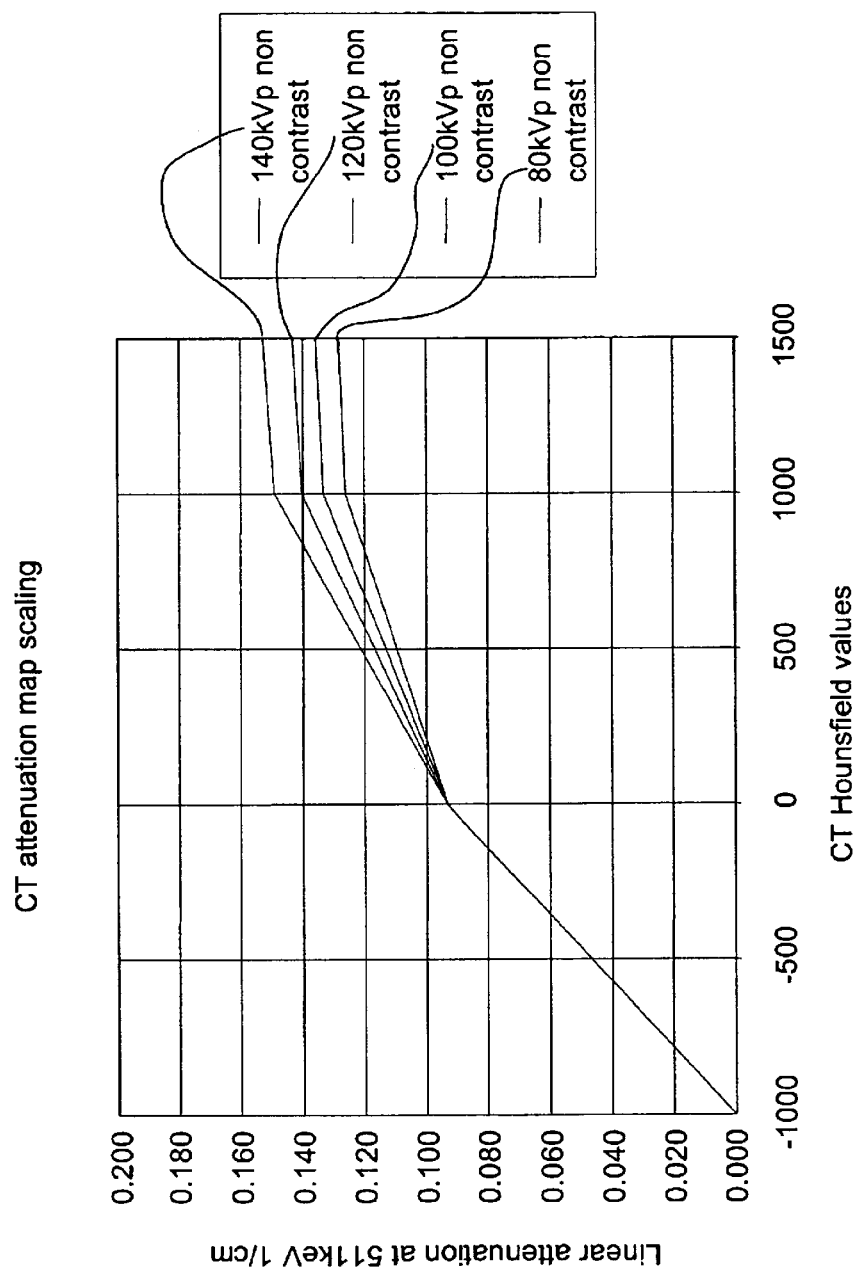
FIG. 15 illustrates a graphical representation of a plurality of conversion tables to convert measurements at different CT kVp settings into attenuation coefficients at 511 keV.

The conversion of the CT numbers to attenuation values can be accomplished by the application of the above described formulae and/or by the use of look up tables which contain an entry for the attenuation corresponding to each CT number. An example graphical representation of the conversion tables to convert measurements at different CT kVp settings into attenuation coefficients at 511 keV is illustrated in FIG. 15.

After the CT values are converted into attenuation values corresponding to the 511 keV photon energy the PET reconstruction proceeds as follows. The attenuation maps are smoothed to match the resolution of the Functional image. Attenuation line integrals are computed through the smoother attenuation maps and sorted into sinograms to match the Functional emission sinograms. The Functional emission data are corrected for attenuation by multiplication by the attenuation correction factors. The corrected Functional data are reconstructed using a tomographic reconstruction such as filtered back projection (FBP) or ordered subset expectation maximization (OSEM).

Figure 16:
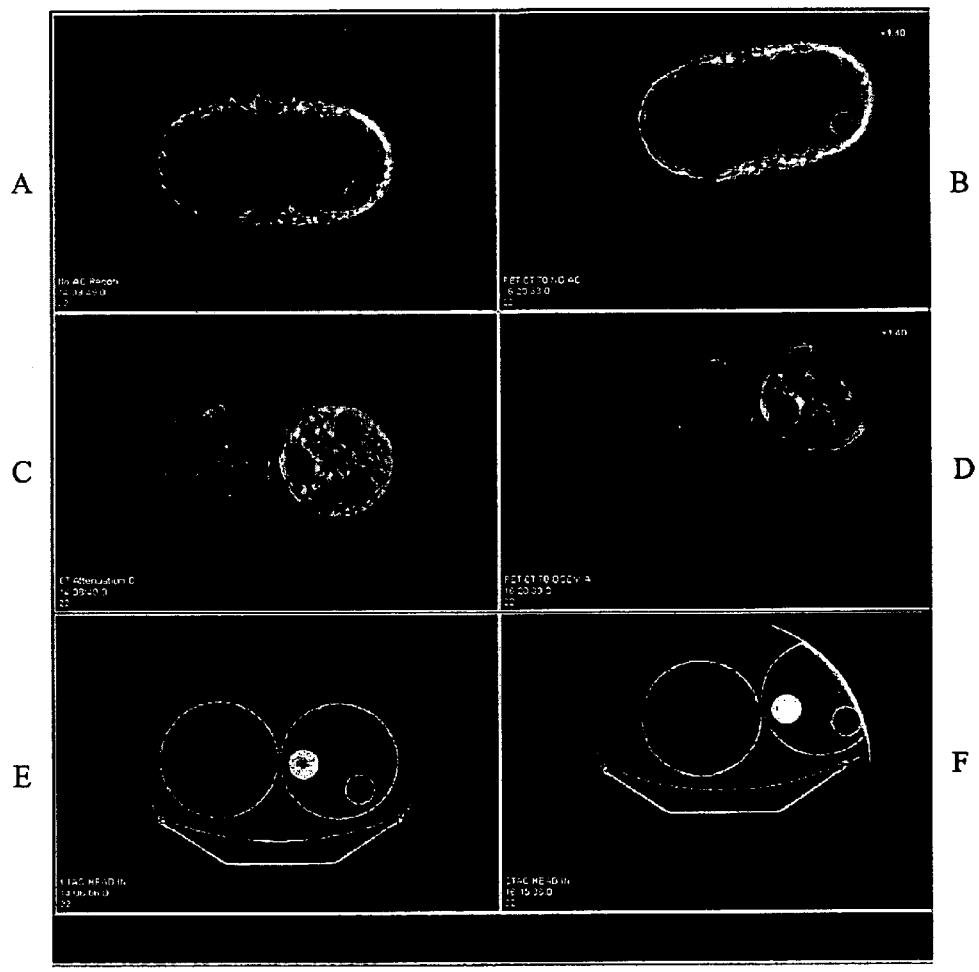
FIG. 16 illustrates example images from the PET CT system shown in FIGS. 1 and 2 where phantoms positioned inside a 50 cm CT FOV are on the left and phantoms positioned outside the 50 cm CT FOV are on the right.

FIG. 16 illustrates example images from PET CT system 10 (shown in FIGS. 1 and 2) where phantoms positioned inside a 50 cm CT FOV are on the left and phantoms positioned outside the 50 cm CT FOV are on the right. A and B represent a PET emission reconstruction with no attenuation correction. In the center row, C and D represent a PET emission reconstruction with attenuation correction from CT, and in the lower row E is a CT image of centered phantoms and F is a CT image from an offset phantom.

Figure 17:
FIG. 17 illustrates activity reconstructed in a truncated attenuation region is lower than in a fully supported region.
Figure 18:
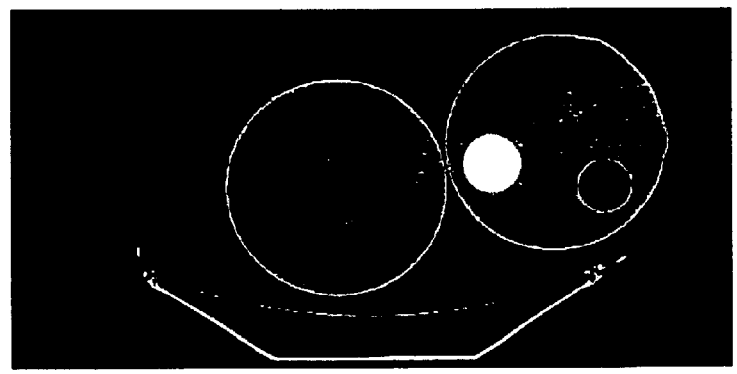
FIG. 18 illustrates CT images reconstructed using detector extrapolation herein described.
Figure 19:
FIG. 19 illustrates a PET emission scan reconstructed attenuation correction derived from an extended CT image.

Two 20 cm diameter, radioactive phantoms were imaged on both PET and CT. Attenuation maps derived from the standard 50 cm FOV images, which have zero attenuation outside the 50 cm diameter, as shown in FIG. 16F, were used to correct the PET emission for attenuation and produce the following emission reconstructions. FIG. 17 illustrates the activity reconstructed in the truncated attenuation region is lower than in the fully supported region (i.e., the partially sampled data). FIG. 18 illustrates CT images reconstructed using the detector extrapolation described previously to produce the extended field reconstruction. A second set of PET reconstructions used attenuation maps derived from the CT data extended over a 65 cm FOV, and FIG. 19 illustrates a PET emission scan reconstructed with attenuation correction derived from the extended CT image.

Herein in at least some cases, the phrase "projection view" is used to refer to a set of image data or attenuation measurements that correspond to parallel trajectories through an FOV where each view includes first through last attenuation measurements corresponding to first through last parallel trajectories. In addition, the phrase "augmented projection view" is used to refer to a projection view that has been altered (see again FIGS. 8 and 9 where curves corresponding to projection views are augmented or extended), typically by adding additional attenuation measurements that correspond to trajectories adjacent either the first or last trajectory in an original view. Similarly, the phrase "un-augmented projection view" is used to refer to projection views to which additional measurements have not been added. The phrase "view attenuation measurement" (see FIG. 6 that shows view attenuation measurements as a function of CT projection angle) is used to refer to the combined attenuation measurements form a single projection view. The phrase "attenuation projection view" is used to refer to a forward projected set of views that is derived from an attenuation map—a 2D image is separated into views. The phrase "attenuation curve" is used to refer to a curve like the one illustrated in FIG. 7 where the attenuation measurements corresponding to a single projection view are plotted so that the curve extends between the first and last corresponding attenuation measurements and so that there are first and second slopes $s_l$ and $s_r$, proximate the first and last attenuation measurements, respectively.

While the invention has been described in terms of various specific embodiments, those skilled in the art will recognize that the invention can be practiced with modification within the spirit and scope of the claims.

What is claimed is:

1. A method comprising:
    scanning an object in a first modality having a first field of view to obtain first modality data including fully sampled field of view data and partially sampled field of view data;
    scanning the object in a second modality having a second field of view larger than the first field of view to obtain second modality data; and
    reconstructing an image of the object using the second modality data and the first modality partially sampled field of view data.

2. A method in accordance with claim 1 wherein said scanning an object in a first modality comprises scanning an object in a first modality to obtain transmission data.

3. A method in accordance with claim 2 wherein said scanning the object in a second modality comprises scanning the object in a second modality to obtain emission data.

4. A method in accordance with claim 1 wherein scanning an object in a first modality comprises scanning an object in a first modality to obtain transmission data comprising Computed Tomography (CT) numbers, said reconstructing an image of the object comprises reconstructing an image of the object using the second modality data and the first modality partially sampled field of view data by converting at least one CT number to a second modality number.

5. A method in accordance with claim 4 wherein converting at least one CT number to a second modality number is based on a x-ray tube voltage.

6. A method in accordance with claim 1 wherein said scanning an object in a first modality comprises scanning an object in a first modality to obtain structural data, said scanning the object in a second modality comprises scanning the object in a second modality to obtain functional data.

7. A method in accordance with claim 1 wherein said scanning an object in a first modality comprises scanning an object in a first modality to obtain fan beam detector data from a plurality of rotation angles around the object, said method further comprises re-ordering the fan beam detector data into sets of data with parallel transmission paths across the field of view.

8. A method in accordance with claim 7 further comprising summing each parallel path set of data to obtain a path attenuation value for each path.

9. A method in accordance with claim 8 further comprising estimating a total integral attenuation of the object using a maximum attenuation path.

10. A method in accordance with claim 9 further comprising estimating an amount of truncated integral attenuation in paths with attenuation less than the maximum attenuation path.

11. A method in accordance with claim 10 further comprising calculating a magnitude and a slope at a point of truncation.

12. A method in accordance with claim 11 further comprising estimating a distribution of a truncated projection using the calculated magnitude and slope.

13. A method in accordance with claim 12 further comprising augmenting the partially sampled field of view data by adding the estimated distribution to the partially sampled field of view data.

14. A method in accordance with claim 1 further comprising providing a delineation in the reconstructed image between areas representative of the fully sampled field of view data and the partially sampled field of view data.

15. An imaging apparatus comprising:
a Computed Tomography (CT) system comprising an x-ray source and a detector responsive to x-rays positioned to receive x-rays emitted from said source;
a Positron Emission Tomography (PET) system comprising a detector responsive to a gamma ray; and
a computer operationally coupled to said CT system and said PET system, said computer configured to:
receive data from a CT scan of an object, the data including fully sampled field of view data and partially sampled field of view data;
augment the received partially sampled field of view data using the fully sampled field of view data;
receive data from a PET scan of the object; and
reconstruct an image of the object using the received PET data and the augmented partially sampled field of view data.

16. An apparatus according to claim 15 wherein said computer further configured to provide a delineation in the reconstructed image between areas representative of the fully sampled field of view data and the augmented partially sampled field of view data.

17. An apparatus according to claim 16 wherein said computer further configured to:
receive a signal representative of an x-ray tube voltage; and
convert at least one CT number to a PET attenuation number based on the x-ray tube voltage.

18. A computer readable medium encoded with a program configured to instruct a computer to:
augment partially sampled field of view data from a first modality using fully sampled field of view data from the first modality; and
reconstruct an image in a second modality using the augmented first modality data.

19. A medium in accordance with claim 18 wherein said program further configured to instruct the computer to:
augment partially sampled field of view Computed Tomography (CT) data using fully sampled field of view CT data; and
reconstruct a Positron Emission Tomography (PET) image using the augmented CT data.

20. A medium in accordance with claim 18 wherein said program further configured to instruct the computer to delineate in the reconstructed image between areas representative of the fully sampled field of view data and the partially sampled field of view data.

21. A method for use with first and second image data sets corresponding to first and second fields of view (FOV), respectively, the first data set including a plurality of projection views that each include first through last attenuation measurements corresponding to first through last parallel trajectories through the first FOV, respectively, the first FOV smaller than and included within the second FOV such that only area common to the first and second FOVs is traversed by each of the projection views and area within the second FOV and outside the first FOV is traversed by only a sub-set of the projection views, the method comprising the steps of:
using the attenuation measurements from at least one projection view to augment the attenuation measurements from at least one other projection view to add attenuation measurements to the at least one other projection view corresponding to trajectories that traverse at least a portion of the second FOV;
using the augmented projection views to compensate the second data set for attenuation; and
combining the compensated second data set to construct an image.

22. The method of claim 21 wherein, for each projection view, the step of using at least one projection view includes summing up all of the attenuation measurements to generate a view attenuation measurement, identifying the maximum view attenuation measurement and augmenting the at least one other projection view as a function of the maximum view attenuation measurement.

23. The method of claim 22 wherein the step of augmenting the at least one other projection view as a function of the maximum view attenuation measurement includes identifying each of the projection views that include at least one of a non-zero first attenuation measurement and a non-zero last attenuation measurement and augmenting each of the identified views.

24. The method of claim 23 wherein the step of augmenting each of the identified views includes, where the first attenuation measurement is non-zero, adding attenuation measurements corresponding to trajectories that traverse at least a portion of the second FOV adjacent the first trajectory and, where the last attenuation measurement is non-zero, adding attenuation measurements corresponding to trajectories that traverse at least a portion of the second FOV adjacent the last trajectory.

25. The method of claim 24 wherein the step of adding attenuation measurements corresponding to trajectories that traverse at least a portion of the second FOV adjacent the first trajectory includes identifying the magnitude of the first attenuation measurement and adding attenuation measurements as a function of the first attenuation measurement magnitude and, wherein, the step of adding attenuation measurements corresponding to trajectories that traverse at least a portion of the second FOV adjacent the last trajectory includes identifying the magnitude of the last attenuation measurement and adding attenuation measurements as a function of the last attenuation measurement magnitude.

26. The method of claim 25 wherein the attenuation measurements that comprise each projection view define an attenuation curve between the corresponding first and last attenuation measurements, the curve defines first and second slopes proximate the first and last attenuation measurements and, wherein, the steps of adding attenuation measurements corresponding to trajectories that traverse at least a portion of the second FOV adjacent the first trajectory includes estimating the first slope and adding attenuation measurements as a function thereof and the steps of adding attenuation measurements corresponding to trajectories that traverse at least a portion of the second FOV adjacent the last trajectory includes estimating the second slope and adding attenuation measurements as a function thereof.

27. The method of claim 26 wherein, for each identified projection view, the steps of adding attenuation measurements include adding attenuation measurements as a function of the relative magnitudes of the first and last corresponding attenuation measurements.

28. The method of claim 27 wherein, for each identified projection view, the step of adding attenuation measurements includes adding measurements such that the combined added measurements is substantially equal to the difference between the maximum view attenuation measurement and the view attenuation measurement corresponding to the identified projection view.

29. The method of claim 28 wherein the first set includes parallel binned CT data and the second set includes PET data.

30. The method of claim 21 wherein the second data set includes data corresponding to a specific energy level and includes second set projection views where each second set view includes measurements corresponding to a plurality of parallel trajectories through the second FOV and, wherein, the step of using the augmented projection views to compensate the second data set for attenuation includes combining the augmented projection views and the un-augmented projection views from the first set to generate an image, converting the image into an attenuation map at the specific energy level, separating the attenuation map into attenuation projection views that correspond to the second set projection views, combining the second set projection views and the attenuation projection views to generate compensated projection views and then combining the compensated projection views to form the image.

31. The method of claim 21 wherein the first set includes parallel binned CT data and the second set includes PET data.

32. The method of claim 21 wherein the first set includes data corresponding to structure of an imaged object and the second set includes data corresponding to functional activity associated with an object.

33. A method for use with a structural data set and a functional data set indicating structural and functional characteristics of an imaged object, the structural and functional sets corresponding to first and second fields of view (FOV), respectively, the structural data set including a plurality of projection views that each include first through last attenuation measurements corresponding to first through last parallel trajectories through the first FOV, respectively, the first FOV smaller than and included within the second FOV such that only area common to the first and second FOVs is traversed by each of the projection views and area within the second FOV and outside the first FOV is traversed by only a sub-set of the projection views, the method comprising the steps of:

for each projection view, summing up all of the attenuation measurements to generate a view attenuation measurement;

identifying the maximum view attenuation measurement; and for each of at least a sub-set of the view attenuation measurements that is less than the maximum attenuation measurement, augmenting the associated projection view to generate an augmented attenuation view such that the sum of all of the attenuation measurements of the augmented view is substantially similar to the maximum attenuation measurement;

using the augmented projection views and the un-augmented projection views to compensate the second data set for attenuation; and combining the compensated second data set to construct an image.

34. The method of claim 33 wherein the attenuation measurements that comprise each projection view define an attenuation curve between the corresponding first and last attenuation measurements, the curve defines first and second slopes proximate the first and last attenuation measurements and, wherein, the step of augmenting projection views includes, for each projection view, determining if the first and last attenuation measurements are non-zero and, for each non-zero first and last attenuation measurement, estimating the magnitude of the attenuation measurement and the slope of the curve proximate the attenuation measurement and adding attenuation measurements corresponding to trajectories that traverse at least a portion of the second FOV to the projection view adjacent the non-zero attenuation measurement.

35. The method of claim 34 wherein, for each identified projection view, the steps of adding attenuation measurements include adding attenuation measurements as a function of the relative magnitudes of the first and last corresponding attenuation measurements.

36. The method of claim 33 wherein the functional set includes data corresponding to a specific energy level and includes functional set projection views where each functional set view includes measurements corresponding to a plurality of parallel trajectories through the second FOV and, wherein, the step of using the projection views to compensate the functional set for attenuation includes combining the augmented projection views and the un-augmented projection views from the structural set to generate an image, converting the image into an attenuation map at the specific energy level, separating the attenuation map into attenuation projection views that correspond to the second set projection views, combining the functional set projection views and the attenuation projection views to generate compensated projection views and then combining the compensated projection views to form the image.

37. A method for use with first and second detectors arranged to collect first and second data sets from a plurality of projection angles about first and second fields of view (FOVs), respectively, the data at each projection angle including a projection view, the second FOV larger than and including the first FOV such that each first set projection view only traverses a portion of the second FOV, the method for generating an image of an object that resides within the second FOV and comprising the steps of:

collecting the first and second data sets;

identifying at least one first set projection view that likely encompasses the entire object as a complete projection view;

where the object extends outside the first FOV:
identifying first set projection views that the object extends out of as truncated projection views;
using the complete projection view data to augment the data of each truncated projection view thereby generating an augmented first set;

combining the augmented first set and the second set to generate a compensated second set; and combining the compensated second set to generate an image.

38. An imaging apparatus for use with a structural data set and a functional data set indicating structural and functional characteristics of an imaged object, the structural and functional sets corresponding to first and second fields of view (FOV), respectively, the structural data set including a plurality of projection views that each include first through last attenuation measurements corresponding to first through last parallel trajectories through the first FOV, respectively, the first FOV smaller than and included within the second FOV such that only area common to the first and second FOVs is traversed by each of the projection views and area within the second FOV and outside the first FOV is traversed by only a sub-set of the projection views, the apparatus comprising:

a computer configured to:
for each projection view, sum up all of the attenuation measurements to generate a view attenuation measurement;
identify the maximum view attenuation measurement; and
for each of at least a sub-set of the view attenuation measurements that is less than the maximum attenuation measurement, augment the associated projection view to generate an augmented attenuation view such that the sum of all of the attenuation measurements of the augmented view is substantially similar to the maximum attenuation measurement;
use the augmented projection views and the un-augmented projection views to compensate the second data set for attenuation; and
combine the compensated second data set to construct an image.

39. The apparatus of claim 38 wherein the attenuation measurements that comprise each projection view define an attenuation curve between the corresponding first and last attenuation measurements, the curve defines first and second slopes proximate the first and last attenuation measurements and, wherein, the computer is configured to augment projection views by, for each projection view, determining if the first and last attenuation measurements are non-zero and, for each non-zero first and last attenuation measurement, estimating the magnitude of the attenuation measurement and the slope of the curve proximate the attenuation measurement and adding attenuation measurements corresponding to trajectories that traverse at least a portion of the second FOV to the projection view adjacent the non-zero attenuation measurement.

40. The apparatus of claim 39 wherein the computer is configured to perform the step of adding attenuation measurements by, for each identified projection view, adding attenuation measurements as a function of the relative magnitudes of the first and last corresponding attenuation measurements.

* * * * *